United States Patent
Fernfors (10) Patent No.: US 6,179,820 B1
(45) Date of Patent: *Jan. 30, 2001

(54) ABSORBENT ARTICLE

(75) Inventor: Ingemar Fernfors, Mölndal (SE)

(73) Assignee: SCA Hygiene Products AB, Gothenburg (SE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/913,718

(22) PCT Filed: Apr. 18, 1996

(86) PCT No.: PCT/SE96/00501

§ 371 Date: Nov. 19, 1997

§ 102(e) Date: Nov. 19, 1997

(87) PCT Pub. No.: WO96/34588

PCT Pub. Date: Nov. 7, 1996

(30) Foreign Application Priority Data

May 3, 1995 (SE) .................................................. 9501619

(51) Int. Cl.[7] .................................................... A61F 13/15

(52) U.S. Cl. ................................ 604/385.27; 604/385.29; 604/385.3; 604/396

(58) Field of Search ..................... 604/385.1, 393–396, 604/385.24–385.3; 2/400, 401

(56) References Cited

U.S. PATENT DOCUMENTS

| 4,425,128 | * | 1/1984 | Motomura | 604/385.2 |
| 4,935,021 | * | 6/1990 | Huffman et al. | 604/385.2 |

FOREIGN PATENT DOCUMENTS

| 0 437 771 | 7/1991 | (EP) . |
| 0 626 160 | 11/1994 | (EP) . |
| 0 694 297 | 1/1996 | (EP) . |
| 2 276 529 | 10/1994 | (GB) . |
| 5076567 | * 3/1993 | (JP) ................................ 604/385.2 |
| 88/00010 | 1/1988 | (WO) . |

* cited by examiner

Primary Examiner—John G. Weiss
Assistant Examiner—K. M. Reichle
(74) Attorney, Agent, or Firm—Burns, Doane, Swecker & Mathis, L.L.P.

(57) ABSTRACT

An absorbent article'such as a pair of absorbent pants, a nappy, an incontinence protection article or the like having a substantially elongated shape is provided. The absorbent article includes a front waist region, a rear waist region and a crotch region positioned therebetween having two leg edge-portions. The absorbent article includes an inner fluid-permeable layer, a fluid-barrier layer and an absorbent core enclosed therebetween. The article also includes elastic elements which are arranged along four different paths. One segment of each path follows at least a portion of a leg edge-portion and the paths together enclose a collection region positioned between the article's leg edge-portions, which region, under the influence of the elastic elements, bulges and forms a fluid-collecting basin.

13 Claims, 3 Drawing Sheets

ABSORBENT ARTICLE

The present invention relates to a fluid-absorbent article intended for disposal after use, such as a pair of absorbent pants, a nappy (diaper), an incontinence protection article or the like with a substantially elongated shape and including a front waist region, a rear waist region and a crotch region therebetween, two leg edge-portions in the crotch region and an inner fluid-permeable layer which is intended to lie against the wearer's skin during use, a fluid-barrier layer which is intended to face away from the user during use and which is substantially impermeable to fluids, and an absorbent core enclosed between the inner layer and the fluid-barrier layer. The article further comprises elastic elements.

BACKGROUND TO THE INVENTION

Fluid absorbent articles such as absorbent pants, nappies, incontinence protection articles or the like normally have an elongated shape with two end portions and an arch-shaped, narrowing mid-portion positioned therebetween, which constitutes the crotch region of the article.

Such articles are normally symmetrical at least about their longitudinal central axis and, in their planar extended state, have an hour-glass contour, whereby the arch-shaped leg edge-portions are adapted to closely envelope the user's thighs during use.

Both of the end portions of the article which form the waist portions are normally provided with a fastening system, or are attached to each other along respective side edges, which creates both a waist-opening as well as two leg openings.

A receiving zone extends between the leg openings in the article's crotch region, the zone being a part of the article which, during wetting, first comes into contact with the excreted fluid. The receiving zone, which is comparatively narrow for anatomical reasons, should be able to receive and absorb large amounts of excreted bodily fluid even over a short time span. During rapid excretion of considerable volumes of urine, for example sudden incontinence in adults, not all the bodily fluid can penetrate sufficiently quickly through the inner layer and be sucked up into the absorbent core. The fluid collects on the surface of the inner layer in the receiving zone and can run out, mainly at the lower parts of the user's groin and along the inside of the thighs, a problem which is often aggravated by the movements of the user. A good sealing of the article's leg openings is therefore particularly sought after.

Such side-leakage does not however only occur due to inadequate sealing around the crotch region. It has shown itself to be the case that even a poor dimensioning of the receiving zone, for instance an abundance of absorption material, as well as a lack thereof, can give rise to undesirable formation of folds in the absorbent core which facilitates an uncontrolled spread of the fluid which is not capable of being absorbed immediately.

It is therefore advocated in the present invention that the receiving zone is given a bowl shape, in which the fluid can be collected at least temporarily until it is able to penetrate into the absorbent core.

Absorbent articles are normally provided with elastic members, primarily along both of the waist portions and around the leg openings in order to improve the anatomical fit of the article. In general these elastic means are fastened in a stretched state to at least the inner layer or to the fluid-barrier layer, either by adhesive, welding, or in another way. In this regard it is also known to provide the leg edge-portions with elastic members arranged in curved paths, with the purpose of creating, during use, a contracting elastic tension around at least a portion of the leg elastics in order to prevent fluid leakage around the user's crutch.

From EP-0,437,771 it is further known to attach elastic elements along two different wave-shaped paths running across the article. A first path follows the frontal portion of the leg edge-portions and a second path follows the rear part of the leg edge-portions. The paths cross each other at the level of the article's lateral central axis in the area of the leg edge portions. The tension in the elastic elements varies along the paths. One disadvantage with such a solution is that those segments of the paths which extend across the article's crotch region exert an undesirable lateral tension in the receiving zone. This results in the risk of folds being formed in the absorbent material and thereby also the risk of side-leakage being imminent. In order to minimize the risk of undesirable formation of folds, EP 0,437,771 advocates that the elastic elements are only attached around the leg edge-portions while the other parts are maintained in an unstretched state. This is however an extremely intricate and expensive way of avoiding the undesirable contraction of the receiving zone.

The British patent GB 2 276 529 discloses a new way of laying out the elastic elements with the purpose of simultaneously obtaining contracting tension forces around both the waist opening and the leg edge-portions. A plurality of elastic elements are arranged along two distinct paths, of which a first path extends from one side edge of the front waist region to the corresponding side edge of the rear waist region and runs therebetween along the opposite leg edge-portion, while the other path describes a corresponding route from the opposite side edge of the article. Such a solution results more unfortunately in considerable disadvantages as soon as it is used. The elastic tensions which are obtained only act on a central part of the leg edge-portions and subject the entire receiving zone to a laterally-directed compression force, whereby the sought-after sealing around the wearer's legs is deficient and unwelcome folds considerably diminish the absorption capacity.

BRIEF SUMMARY OF THE INVENTION

Much trouble has thus been spent on producing an article where the leg and waist openings are sealed but still comfortably tight-fitting around the user's waist and legs, so that leakage of bodily fluid out of the article is prevented. Despite this, no completely satisfactory solution to the problem has been put forward.

The basic idea of the invention is, by means of a suitable distribution of elastic forces over the surface of the article, both to create a bowl-formed container in the receiving zone, for collection of fluid and faeces, as well as to create contracting forces around the contours of the leg edge-openings in order to give a good seal against the user's legs. In accordance with the invention it is possible to make use of elastic forces also in the absorbent article's receiving zone so that, in a controlled manner, bowl-like structures for collection of urine and faeces are created.

An article produced in accordance with the invention is primarily identifiable by elastic elements being attached along four different paths, of which a first path and a second path extend from one side edge of the front waist region to the opposite side edge of the rear waist region and cross the article's longitudinal central axis on their respective side of the receiving zone. A third path and a fourth path are mirror images of the first and second paths with respect to the article's longitudinal central axis. The first path follows the rear part of one of the leg edge-portions while the second path follows the opposite leg edge-portion's frontal part. The paths intersect each other at four different intersections, two of which lie on the article's longitudinal central axis and the other two of which lie in the vicinity of the leg edge-portions, each one being on one side of the absorbent core. The paths thus enclose an area of the receiving zone which bulges under the influence of the elastic elements and forms a bowl-shape.

Said another way, the present invention provides a fluid absorbent article intended for disposal after use, that is a pair of absorbent pants, a nappy, or an incontinence protection article. The article has a substantially elongated shape and includes a front waist region, a rear waist region and a crotch region therebetween. The crotch region has two leg edge-portions. The article further comprises an inner fluid-permeable layer which is intended to lie against a user's skin during use, a fluid-barrier layer which is intended to face away from the user during use and which is substantially impermeable to fluids, and absorbent core enclosed between the inner layer and the fluid-barrier layer. The article further comprises elastic elements, wherein the elastic elements are attached along at least four different paths, and in that a first path and a second path extend from the front waist region to the rear waist region, from a side of a central longitudinal axis of the article to an opposite side of the article's central longitudinal axis, and in that the first path and the second path intersects the article's central longitudinal axis at different locations, and in that a third path and a fourth path are mirror images of the first path and second path, respectively, with respect to the article's longitudinal central axis. A segment of each path follows at least a part of a leg edge-portion, and the paths together enclose a collection region positioned between the article's leg edge-portion, which region, under the influence of the elastic elements, bulges and forms a fluid-collecting basin. The elastic elements are attached in a stretched condition along each path including being attached in the stretched condition along said portions of all said paths enclosing the collection region.

According to one embodiment of the invention, at least two elastic strips are attached in a pre-tensioned condition along each of the four paths.

According to another embodiment of the invention, the first and second paths extend from a portion of the front waist area on one side of the article's central longitudinal axis to a portion of the rear waist region on the opposite side of the article's longitudinal central axis. The third and fourth paths run in a mirror image of the first and second paths with respect to the central longitudinal axis of the article.

According to a further embodiment, the first and second paths extend from the end edge of the front waist portion around the article's central longitudinal axis to the end edge of the rear waist portion on the opposite side of the article's central longitudinal axis. The third and fourth paths run in a mirror image of the first and second paths with respect to the central longitudinal axis of the article.

An especially advantageous tensile force distribution is obtained by attaching the elastic elements in a pre-tensioned state along four different curved paths. Two of the paths cross through the middle portion of the article from one side edge of the front waist region to the opposite side edge of the rear waist region with a varying separation in the article's lateral direction. The two other paths run from one side edge of the rear waist region to the opposite side edge of the front waist region with corresponding separation, i.e. as a mirror image of the first two with respect to the article's central longitudinal axis, The paths intersect each other at four different points, two of which lie on the article's central longitudinal axis, each on their own side of the central part of the absorbent core, and two lie on either side of the article's central longitudinal axis in the vicinity of each leg edge-portion. These four intersection points are combined with four curved segments, which together enclose a region of the receiving zone, the article's collection region. Its contours are bordered by elastic elements which exert a contracting tension around the whole of the periphery of the collection region. Since the tension is transferred from the elastic elements to the absorbent core, this tends to bulge and rise up along the contour of the collection region, this creating a bowl-shaped basin for collection of fluids and faeces.

The invention will now be described in more detail with reference to embodiments depicted in the accompanying drawings.

DESCRIPTION OF EMBODIMENTS

An article for the collection of urine or faeces which is particularly representative for the invention has been chosen as an embodiment, namely a pair of absorbent pants, primarily intended to be worn by adult persons who suffer from incontinence, for example sudden-incontinence.

The absorbent pants comprise a front waist portion 2 intended to contact the user's stomach during use, a rear waist portion 3 intended to be in contact behind the user's back and a crotch region 4 positioned between the front and rear waist regions. The crutch region is intended to cover the comparatively narrow space of the user's lower pelvis between the groin creases and the inside of the thighs.

In order to be described more easily, the absorbent pants 1 are shown in a planar extended state, i.e. not attached in the form of a pair of pants. In reality the absorbent pants do not look like this, neither when they are being taken out of a packet nor when they are in use. In these instances the absorbent pants instead resemble a pair of normal, somewhat thick, underpants. The extended state in FIG. 1 may however possibly be present during production of a pair of absorbent pants according to the invention.

The crotch region 4 of the absorbent pants 1 is normally narrower than the waist regions 2, 3. The side edges of the crotch region gradually converge from the front waist region to the article's narrowest portion which is somewhat displaced with respect to the article's lateral central axis, whereafter the width of the crotch region increases successively towards the rear waist portion. The side edges of the crotch region are to follow the shape of the user's trunk from the front part of the hips along the converging lines of the groin creases to the inside of the thighs and thereafter diverge around the rear part of the thighs and up to the rear part of the hips. In the extended state, the absorbent pants 1 thus present the contours of a somewhat asymmetrical hourglass around the central lateral axis X—X.

Each waist region 2, 3 has two side edges orientated in the article's longitudinal direction and one end edge extending in the article's lateral direction. The frontal end edge 18 and the rear end edge 29 are preferably the same length. The side edges of the waist regions extend by the same amount in the shown embodiment.

The crotch region 4 of the absorbent pants is longer in the article's length direction than each waist region 2, 3, The length of the crotch region 4 suitably constitutes between half and three-quarters of the article's 1 total length, preferably about two thirds of the article's total length. The crotch region 4 is narrower than the other parts of the article and its smallest part suitably constitutes about one third of the article's total width. The lateral dimension of the absorbent pants 1 is constant in the waist area. The side edges of the crotch region 4 assume an even concave arc on either side of the article's central longitudinal axis; an arc which basically describes a semi-circle or a half-ellipse and is dimensioned to surround the user's thighs during use. The absorbent pants 1 are made up of three different layers 7, 8, 20 and absorbent core 9. The absorbent pants thus comprise an inner, fluid-permeable layer (sheet) 7 of, for example, hydrophillic fibrous material, so-called "non-woven", comprising fibres of e.g. polyethylene, polypropylene, polyester or mixtures of these, which inner layer 7, during use, faces inwardly towards the side of the absorbent core 9 directed towards the user. The inner layer 7 might also consist of, or comprise, viscose fibres or it might be constituted by a perforated plastic film, a plastic net, or a sheet of fluid-permeable foam material.

Additionally, the absorbent pants present a fluid-impervious, or at least fluid-repelling fluid-barrier layer 8 of plastic material, for example polyethylene or a hydrophobic fibre material, possibly a fibre material which has been suitably impregnated, or alternatively another suitable material, said fluid-barrier layer 8 being intended to be affixed to the side of the absorbent core 9 which, during use, faces away from the user. A third layer 20, in the following referred to as the outer layer 20, of fibre material or the like for example, is fastened or laminated onto the side of the fluid-barrier layer 8 which faces away from the absorbent core 9. The outer layer 20 has the primary purpose of giving the outside of the absorbent pants 1 a textile-like guise, at least to the touch but also to a certain extent with respect to its appearance.

The absorbent pants 1 also comprise, as already mentioned, an elongated absorbent core 9 in the longitudinal direction of the article, the core 9 being enclosed between the inner layer 7 and the outer layer 20. The extent of the inner layer 7 coincides with the total extent of the absorbent pants and is joined, by means of adhesive, heat-sealing, ultra-sound welding or another suitable conventional method, to the fluid-barrier layer 8 and to the outer layer 20. The layers 7, 8, 20 are joined over the surfaces which extend outside the absorbent core 9 and together thereby form an envelope which encloses the absorbent material. The absorbent core 9 can for example contain cellulose fibres and can even comprise other absorbent materials such as polymeric hydrocolloidal materials, in particle form for example. Such materials, generally known under time name "superabsorbents" have the capacity to absorb many times their own weight of fluid. The absorbent core 9 can also contain non-absorbent materials such as thermoplastic fused-fibres having the purpose of strengthening the absorbent core 9 or improving its tendency to spring back after having been subjected to compression in a package, or in connection with use. The absorbent core 9 can advantageously by made up of a plurality of different layers of absorbent material, or of different regions which present mutually different characteristics with regard to their capacity for absorbing, spreading and storing fluid. The absorption speed can be raised in the receiving zone by a suitable choice of fibre structure, while the capacity to store and retain fluid can be improved in parts of the absorbent core 9 which do not lie in direct contact with the receiving zone and towards which fluid can be spread, by using a higher amount of superabsorbent.

Figure 1:
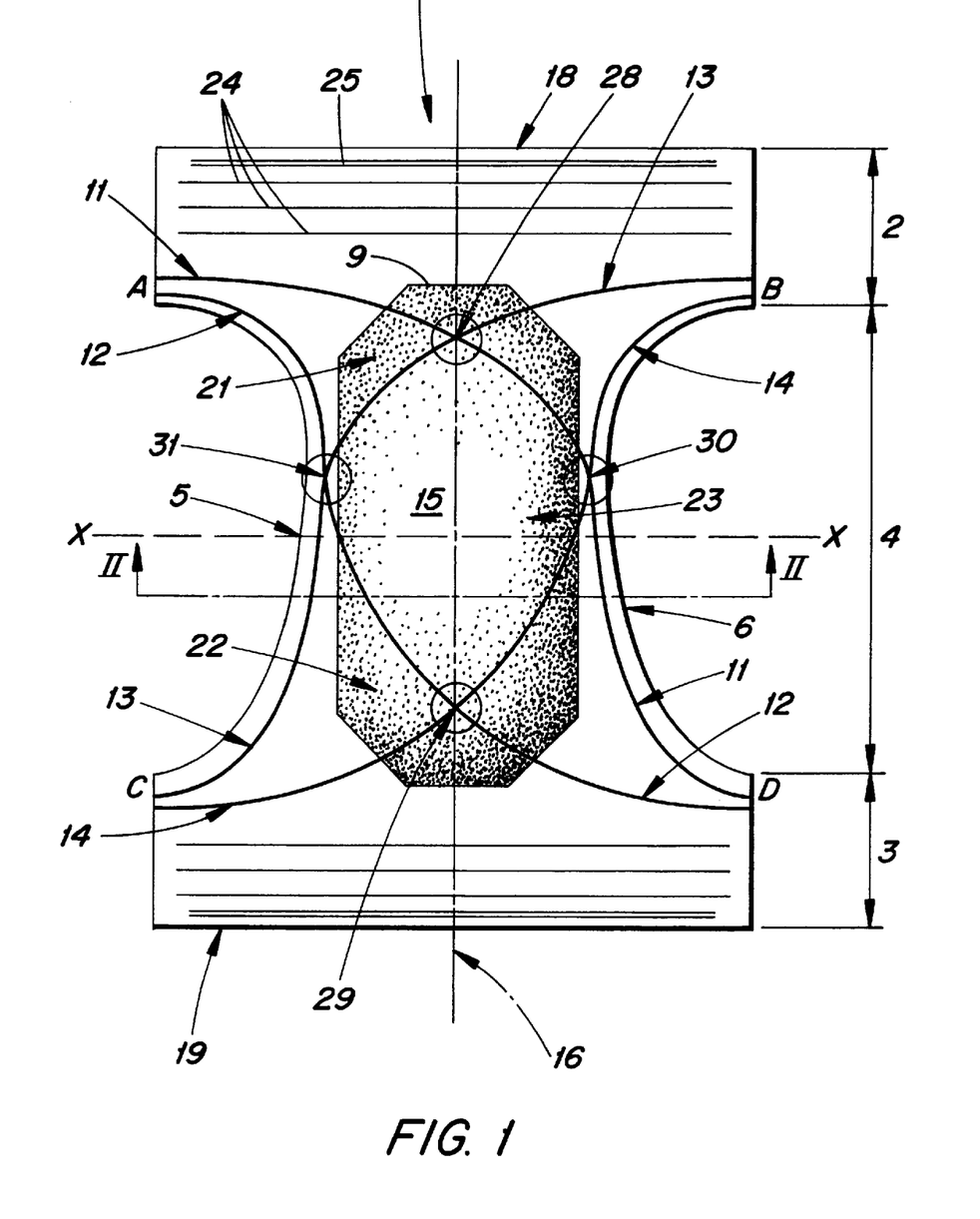
FIG. 1 of the drawings depicts a pair of absorbent pants in a planar extended state, said absorbent pants not having been attached together into their pants form, and with the inner layer 7 removed for clarity.
Figure 2:
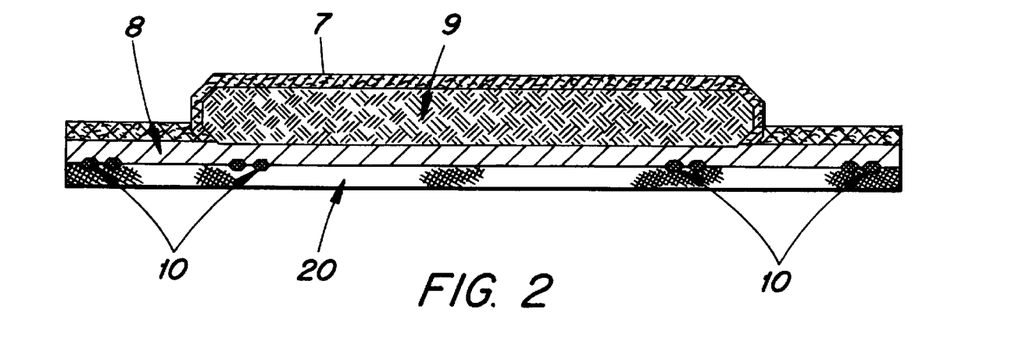
FIG. 2 shows a cross-section of the same absorbent pants along line II—II in FIG. 1, without inner layer 7 removed.
Figure 3:
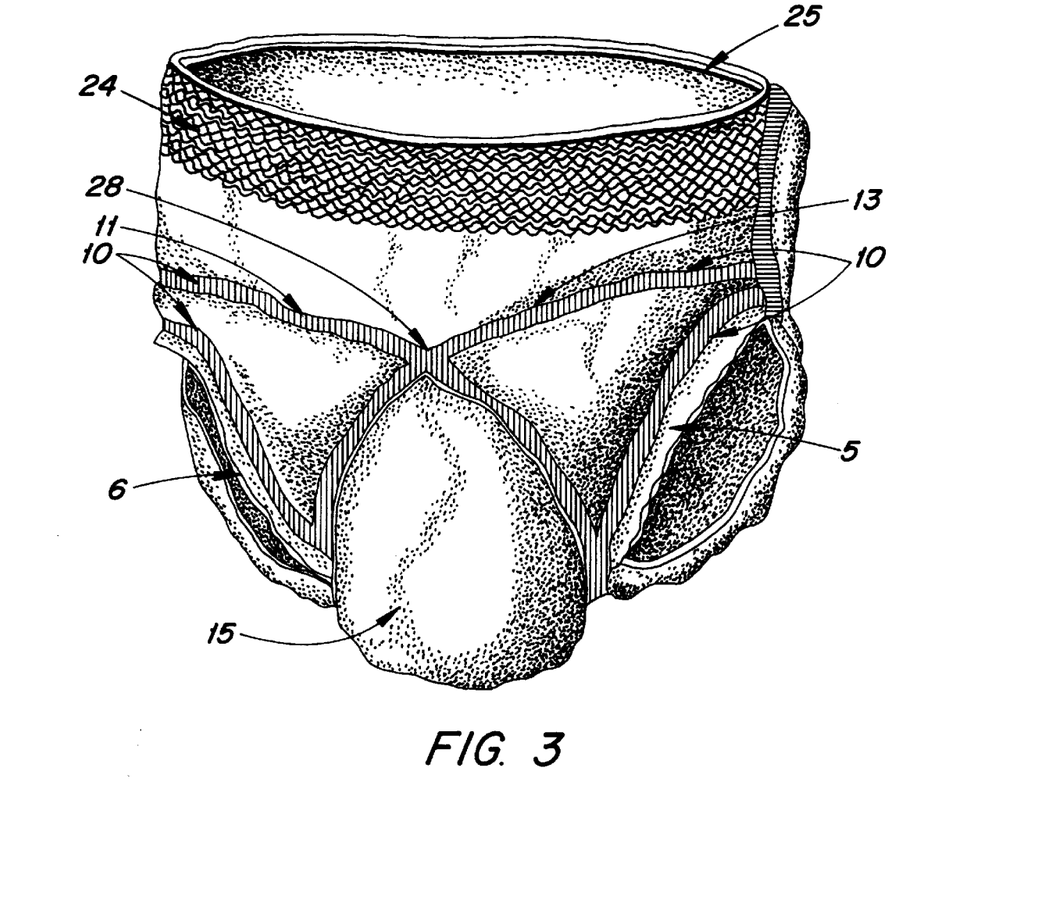
FIG. 3 shows the absorbent pants in a condition of use.

The absorbent core 9 further presents a front end portion 21, a rear end portion 22 and a central portion 23 positioned therebetween, two side edges and two end edges. The shape of the absorbent core is substantially rectangular, possibly with somewhat wider end portions 21, 22 and a somewhat narrowing central portion 23 in comparison thereto. The absorbent body 9 is narrower and shorter than the inner layer 7 and suitably, as shown in FIG. 1, displaced forwardly in the absorbent pants 1, whereby the front end portion 21 of the absorbent core 9 extends over a part of the front waist portion 2 of the absorbent pants i and the absorbent core's central portion 23 is arranged in the crotch region 4 of the absorbent pants.

The fluid-barrier layer 8 does not have to have the same extent in the lengthwise direction as the inner layer 7, but instead can extend only to a point just outside the end edges of the absorbent core 9, whereby large parts of the rear portion of the absorbent pants are not covered by fluid-proof material, which is something which allows and facilitates air permeability through these parts. The fluid-barrier layer 8 can of course extend over substantially the total area of the article in order to ensure a better protection against leakage. In such a case, the outer fluid-impervious layer 8 should consist of an air-permeable and vapour-permeable material or should be provided with perforations over parts of the regions which do not cover the absorbent core 9.

The textile-like outer layer 20 and the fluid-barrier layer 8 are suitably united with one another over the whole common area of the layers, by lamination using any suitable conventional method, such as gluing, heat-sealing, ultrasound welding, extrusion-coating or similar. The textile-like rear layer consists of a vapor-permeable material and extends over the whole rear side of the article. The inner layer 7 and the outer layer 20 can be constituted of like materials and be connected with each other over those parts of the article which extend outside the absorbent core 9.

A plurality of elastic elements 24, for example threads, strips or the like are attached in a stretched state across the front as well as the rear waist region 2, 3. The number of elastic elements 24 can vary and is by no means limited to that depicted in the figures. The elastic elements 24 are continuously or intermittently attached with adhesive, or attached in another suitable way, between the inner layer 7 and the textile-like outer layer 20, or joined to at least one of the inner layer 7, the fluid-barrier layer 8 or the outer layer respectively, across the frontal waist region 2 and the rear waist region 3.

In accordance with an alternative embodiment, the inner layer 7 is folded over along the article's end edges 18, 19, over the whole of, or at least part of, the waist regions 2, 3, whereby the elastic elements 24 are attached in the fold which is thereby formed in the inner layer 7.

By means of the elastic elements 24, both the waist regions 2, 3 of the absorbent pants 1 are given an elasticity and stretchability such that, during use, they sealingly surround the user's waist in a close and pliant manner. Instead of the elastic threads or strips, a sheet or a net of elastically extensible material, such as an elastic fiber material or foam material, can of course be laminated over at least parts of the two waist regions 2, 3. Such an elastically extensible film can for example comprise ethylene-vinyl-acetate, ethylene-acrylic acid, ethyl-butyl-acetate, polyurethane, styrene-butadiene, polybutadiene, polyisoprene, isoprene rubber or ethylene-propylene rubber.

The waist regions 2, 3 of the absorbent pants further comprise elastic elements 25, attached along respective end edges 18, 19 of the article. These elements 25 can also be pre-tensioned attached threads, strips or the like. They however preferably exhibit larger stretching and contraction forces than the separate elastic elements in the aforementioned elasticated stretchable waist regions 2, 3. As an alternative to providing the waist regions 2, 3, with elastic elements 24, 25, the waist regions 2, 3 can be constituted by an elastically stretchable material.

The absorbent pants 1 further comprise an array of elastic elements which also extend in the article's central portion 4 and which basically have the purpose of creating sealing edges surrounding the user's legs in use and also forming a bowl-shaped region in the middle of the absorbent pants crotch region 4, intended to collect excreted fluid. The bowl-shaped region coincides substantially with the so-called receiving zone/region of the absorbent pants, which is the part of the absorbent pants' crotch region 4 which during use is first wetted by the bodily fluid excreted into the article.

The crotch region 4 of the absorbent pants presents two side edges 5, 6, which are substantially semi-circularly, or semi-elliptically, curved in a concave manner with respect to the central longitudinal axis of the article, said edges 5, 6 constituting the article's first and second leg edge-portions 5, 6. The crotch region 4 of the absorbent pants also presents four corners A, B, C, D; namely a first corner A positioned on the borderline between the first side edge of the front waist region 2 and the first leg edge-portion 5; a second corner B positioned on the borderline between the second side edge of the frontal waist region and the second leg edge-portion 6; a third corner C positioned on the borderline between the first side edge of the rear waist region 3 and the first leg edge-portion 5, as well as a fourth corner D positioned on the borderline between the second side edge of the waist region 3 and the second leg edge-portion 6.

Elastic elements 10 are attached along at least four different curved paths 11, 12, 13, 14, of which a first path 11 and a second path 12 extend from the first side edge of the front waist region to the opposite side edge of the rear waist region, from a point close to the first corner A to a point close to the fourth corner D, i.e. basically diagonally over the article's crotch region 4 along different routes from the frontal part of the first leg edge-portion 5 to the rear part of the second leg edge-portion 6. A third path 13 and a fourth path 14 run from the first side edge of the rear waist region to the opposite side edge of the front waist region, from a point close to the third corner C to a point close to the second corner B, i.e. basically diagonally over the article's central region 4 along different routes from the rear part of the first leg edge-portion 5 to the frontal part of the second leg edge-portion 6.

The first path 11 extends, as can best be observed in FIG. 1, from a point close to the first corner A in an evenly-curved arc to an intersection point 28. The first path 11 and the third path 13 meet at the intersection point 28 which is positioned on, or in the immediate vicinity of, the article's central longitudinal axis 16 on a level with the front portion 21 of the absorbent core. The first path 11 thereafter curves from the intersection point 28 towards the other leg edge-portion 6 and crosses the fourth path 14 at its point of inflection 30, positioned close to the second leg edge-portion 6 on a level with the article's narrowest portion. By point of inflection is meant the point where the radius of curvature of a curve changes sign, i.e. where the curvature of the curve shifts from being convex to concave, or vice-versa.

The first path 11 substantially follows the rear part of the second leg edge-portion 6 from the point of inflection 30, along the arc-shaped contour up to a point close to the fourth corner D.

The second path 12 basically follows the front portion of the first leg edge-portion 5, along its arc-shaped contour, from a point near to the first corner A to a point of inflection 31 positioned close to the border of the first leg edge-portion 5, on a level with article's narrowest part. Both points of inflection 30, 31 lie at the same level on either side of the article's central longitudinal axis 16.

The second path 12 crosses the third path 13 at the point of inflection 31 and then curves in a direction towards the article's central longitudinal axis 16. The second path 12 crosses the fourth path 14 at an intersection point 29 positioned on, or in the immediate vicinity of, the article's central longitudinal axis 16 on a level with the rear portion 22 of the absorbent core, whereafter the second path curves to a point close to the fourth corner D.

The third path 13 is a mirror image of the first path 11, or more precisely expressed is a 180° rotation of the first path 11 around the article's central longitudinal axis 16. The fourth path 14 is similarly a 180° rotation of the second path 12 around the article's central longitudinal axis 16.

Consequently the four paths 11, 12, 13, 14, in FIG. 1 form a configuration in accordance with the following:

The first path 11 starts in the article's lateral direction from the first side edge of the front waist region 2, at the frontal portion of the first leg edge-portion 5 and then curves continuously, i.e. deviates gradually from the lateral direction, to its point of inflection 30. At the point of inflection 30, the direction of path 11 is tangential to the contour of the leg edge-portion 6, after which the path 11 curves around the rear part of the second leg edge-portion 6 to the second side edge of the rear waist region 3 where the path is again directed laterally to the article. At its point of inflection 30, the path forms an angle of between 45 and 90 degrees, preferably between 60 and 80 degrees, to the article's lateral direction. The second path 12 starts in the article's lateral direction from the first side edge of the front waist region and curves around the frontal part of the first leg edge-portion 5 to its point of inflection 31 which is positioned close to the first border of the first leg edge-portion 5 on the same level as the point of inflection 30 of the first path 11.

The first and second paths 11, 12, basically have the same direction at respective points of inflection 30, 31. The second path thereafter curves over tire rear portion of the absorbent core to the second side edge of the rear waist region. The third path and the fourth path 13, 14, are mirror images of the second and first path 12, 11, respectively.

At least a part of each path runs over the absorbent core. The first path 11 crosses the fourth path 14 outside the side edge of the absorbent core at the point of inflection 30. The second path 12 crosses the third path 13 outside the opposite side edge of the absorbent core at the point of inflection 31. The first and the third paths 11, 13 have their intersection point 28 in the frontal part 21 of the absorbent core and the second and fourth paths 12, 14 have their intersection point 29 in the rear part 22 of the absorbent core. In this way, the four different paths 11, 12, 13, 14 enclose a region 15 positioned in the article's crotch region 4, which region 15 basically has the form of a rhombus with convex curved sides and which is determined by the four points 28, 30, 29, 31.

The above-defined, curved rhombus-shaped area of the receiving zone is symmetrical about the article's central longitudinal axis. The short diagonal of the rhombus extends in tile article's lateral direction over the narrowest part of the crotch region between the leg edge-portions 5, 6, while its long diagonal runs over the absorbent core along the article's central longitudinal axis between the front and rear part of the absorbent core. This curved rhombus-shaped region constitutes the article's collection region 15 and is intended, during use, to temporarily retain the portion of the fluid which is not immediately taken up by the absorbent material.

It is therefore desirable to give the collection region 15 a bulging bowl-shape primarily for preventing the fluid from running out sideways towards the leg edge-portions 5, 6. One or more elastic elements 10 such as threads, strips or the like are attached in a pre-tensioned state substantially along the four different paths 11, 12, 13, 14 and these exert a contracting tension directed towards the respective radii of curvature.

In a preferred embodiment, the two elastic elements 10, for example consisting of flat elastic strips, are arranged along each path, said elements being joined to at least one of the layers 7, 8, 20. The strips are preferably attached between the fluid-barrier layer 8 and the outer textile-like layer 20 and tensioned over its whole extent. The strips are continuously, or intermittently, fixedly adhered to at least the outer textile-like layer 20. The strips can of course be affixed with other conventional methods.

The elastic strips can also be attached to the inside of the article, i.e. on the side of the inner layer 7 which faces the absorbent core 9, which is something that gives rise to certain advantages with regard to the desire of giving the collection zone 15 an outwardly-bulging shape, but which however increases the risk of skin irritation.

Figure 4:
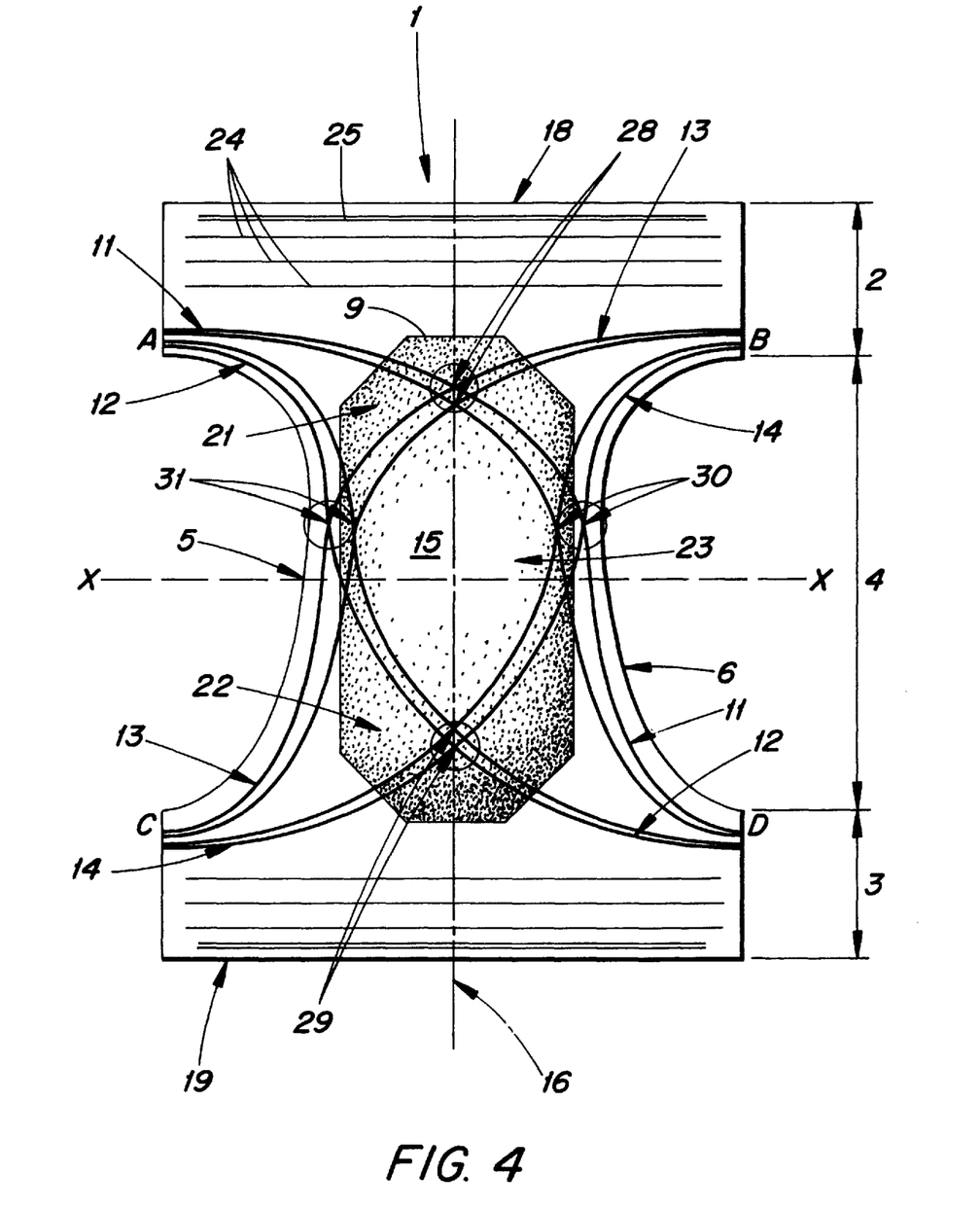
FIG. 4 shows a pair of absorbent pants in a planar extended state, having inner layer 7 removed for clarity.

In a preferred embodiment, at least two elastic threads or strips are attached to the side of the outer, textile-like sheet 20 which faces the fluid-barrier layer 8. The separation distance of the strips can be constant or it can vary along the respective path. In a preferred case, the separation distance of the strips varies proportionally with ah i angle which the path forms with the article's lateral direction, as illustrated in FIG. 4. The separation distance between the strips consequently has its greatest value at the path's respective point of inflection where the strips can be separated by an amount of between one millimeter up to many centimeters, preferably between three millimeters and fourteen millimeters. Said another way, the separation distance of the elements in the respective path, measured perpendicular to the elements at a given point on the path, is proportional to an angle which is formed between the article's lateral direction and a path tangent at the given point. In the vicinity of the side edges of the waist regions 2, 3 the separation distance is suitably reduced.

In an alternative embodiment, a plurality of elastic strips can be arranged along each path. The distance between the innermost and outermost strips running along one and the same path should then be sufficiently large in order to raise up the leg edge-portions towards the inside of the article and thereby form leakage barriers on either side of the absorbent core.

The different elastic elements which run along one and the same path may additionally be attached with different tensions, or may be pre-tensioned with varying tensions in different segments of tile path. The points of inflection 30, 31 do not have to be positioned outside the absorbent core's side edges but can just as well be positioned inside these. In the same way, the intersection points 28, 29 can lie outside the end edges of the absorbent core or in respective waist regions.

At least one of the different elastic elements which run along one and the same path can, in those places where the path is tangential to the edges of the absorbent core, extend inside the absorbent core whilst the remaining elements run outside of this.

The collection region 15 is, as already stated, surrounded by four segments of elastic paths 11, 12, 13, 14 and thereby also bordered by the pre-tensioned attached elastic elements 10 which exert a contracting force along its whole contour. In this way a closed elastic circuit is created which tends to be drawn together into its relaxed state. Whether the elastic elements 10 are arranged on the outside or the inside of the absorbent core 9, the same will bulge under the influence of the elastic circuit's contracting force. At each point, the contracting elastic force is directed along the path and consequently has a tangential component and a radial component directed perpendicularly to this. The former is directed along the path's tangent at the point of action and the latter points along the radius of curvature. The tangential components cooperate in order to shrink the perimeter of the collection region. Since the edges of the collection region are curved in a convex manner, all of the radial force components act towards the interior of the collection region.

Since the elastic elements are directly or indirectly united with the absorbent core's flexible material, the force can be transferred to the same. For example, at the intersection points 28 and 29, the resultant of the cooperating radial force components from the paths 11 and 13 and 12 and 14 respectively will point along the article's central longitudinal axis towards the center of the collection region. In the same way, one can easily be assured that the resultant forces from the cooperating radial components at the points of inflection 30 and 31 will point in the lateral direction towards the center of the collection region.

Since the collection region is symmetrical, the radial force components from both sides cancel out each other along the article's central longitudinal axis, along which the absorbent core folds together in the lateral direction under the influence of the tension, at the same time as the absorbent core also curves in the lengthwise direction. In this way the collection region's 15 area tends to bulge and form a canoe-shaped basin between the leg edge-portions 5, 6. In the same way, the leg edge-portions 5, 6 are bordered by elastic elements which are intended, during use, to exert a contracting force around the user's legs.

The absorbent pants, as mentioned earlier, have up until now been described in their non-joined state, a state in which the waist regions are not combined with one another. A waist opening and two leg edge-portions are created by folding the article about its central lateral axis in such a way that both end edges coincide. In this way the first and second side edges of the front waist region are made to coincide with the first and second side edges respectively of the rear waist region. By securing together the waist regions along the side edges a finished pair of absorbent pants is obtained which very closely resembles an ordinary pair of underpants in shape and appearance. The material around the waist opening is elastically stretchable in at least the articles's lateral direction, due to the lateral elastic elements 24, 25. The frontal part of the first leg edge-portion is surrounded by parts of the second and third paths 12, 13 which are united at one of the waist opening's joints. In the same way, the second leg edge-portion is surrounded by parts of the first and fourth paths 11, 14, which are united at the waist opening's second joint.

The invention is of course not limited to the above-described embodiments. Other ways of depicting the basic idea behind the invention are described in the following with reference to the figures.

As concerns the production of the article, the invention is extraordinarily well-suited to lateral production, i.e. production in which a running web of material from which the articles are formed is displaced substantially in the article's lateral direction. In this way, the elastic elements are arranged along four different wave-formed, paired, mirror-image paths. The invention can also be applied in longitudinal production. This is intended to mean production in which a running web of material, from which the articles are formed, is displaced substantially in the article's lengthwise direction. In such a case, the elastic paths will extend from the article's one end edge to the opposite end edge and will otherwise be arranged according to basically the same configuration as in the preceding embodiment.

In an alternative embodiment, the elastic elements can be arranged along substantially straight lines, or along one of a plurality of essentially straight segments forming a combined run, possibly with rounded corners. A characteristic of the elastic paths, whether they be straight or curved, is that they start at one side of the article and run to the opposite side, i.e. that they intersect the article's central longitudinal axis and that each path is at least tangential to the contour of the frontal part or the rear part of one of the leg edge-portions, in such a way that both said contours will be tangential at at least one position of its frontal part and one position of its rear part. The term "be tangential" should be understood here to be such that the path has at least one point which borders the leg edge-portion's contour, without it necessarily having to coincide with this. This implies that a first path can extend from the frontal part of one side of the article and be tangential to the front part of the first leg edge-portion while a basically mirror-image path extends from the frontal part of the article's opposite side and is tangential to the frontal part of the other leg edge-portion. In the same way, a third path runs from the rear part of one side of the article and is tangential to the rear part of the first leg edge-portion, at the same time as a fourth path, substantially a mirror-image, runs from the rear part of the article's opposite side and is tangential to the rear part of the second leg edge-portion. The paths can be parallel in pairs, at least over a part of the article's crotch region. If the paths are straight, they will together form a rhombus or a parallelogram in the article's receiving zone, with one diagonal directed along the article's central longitudinal axis.

The elastic elements can additionally be attached in a configuration where the front intersection point 28 is positioned in the frontal waist region and the rear intersection point is in the rear waist region, whereby the elastic elements also contribute to creating contracting forces around the waist opening.

What is claimed is:

1. A fluid-absorbent article intended for disposal after use, that is a pair of absorbent pants, a nappy, or an incontinence protection article, with a substantially elongated shape and including a front waist region, a rear waist region and a crotch region therebetween, said crotch region having two leg edge-portions, the article further comprising an inner fluid-permeable layer which is intended to lie against a user's skin during use, a fluid-barrier layer which is intended to face away from the user during use and which is substantially impermeable to fluids, and an absorbent core enclosed between the inner layer and the fluid-barrier layer, said article further comprising elastic elements, wherein the elastic elements are attached along at least four different paths, and in that a first path and a second path extend from the front waist region to the rear waist region, from a side of a central longitudinal axis of the article to an opposite side of the article's central longitudinal axis, and in that the first path and the second path intersect the article's central longitudinal axis at different locations, and in that a third path and a fourth path are mirror images of the first path and second path, respectively, with respect to the article's longitudinal central axis, and in that a segment of each path follows at least a part of a leg edge-portion, and portions of all the paths together enclose a collection region positioned between the article's leg edge-portions, which region, under the influence of the elastic elements, bulges and forms a fluid-collecting basin, the elastic elements being attached in a stretched condition along each path including and being attached in the stretched condition along said portions of all said paths enclosing the collection region.

2. The article according to claim 1, wherein the first path and the second path extend from a side edge of the front waist region to an opposite side edge of the rear waist region.

3. The article according to claim 1, wherein the first path runs around at least a portion of a front part of one of said leg edge portions whilst the second path runs around at least a portion of a rear part of an opposite one of said leg edge portions.

4. The article according to claim 1, wherein the first path and the second path each intersect the article's central longitudinal axis on a different side of a central part of the absorbent core, and in that the collection region extends in a lengthwise direction between two intersection points defined thereby.

5. The article according to claim 1, wherein the second path and the third path intersect one another close to one of the leg edge-portions, and in that the first path and the fourth path intersect one another close to an opposite one of said leg edge portions, and in that the collection region extends in the lateral direction between intersection points defined thereby.

6. The article according to claim 1, wherein the second path and the third path intersect one another outside a side edge of the absorbent core, and in that the first path and the fourth path intersect one another outside an opposite side edge of the absorbent core.

7. The article according to claim 1, wherein the first path extends around a back part of the second leg edge-portion at least from the intersection point between the first path and the fourth path, to a corresponding side edge of the rear waist region, and in that the second path extends around a front part of the first leg edge-portion from a corresponding side edge of the front waist region at least to the intersection point between the second path and the third path.

8. The article according to claim 1, wherein at least two elastic elements are attached in a stretched condition along each path, and in that a separation distance between the elements varies along each path.

9. The article according to claim 8, wherein the separation distance of the elements in a respective path, measured perpendicular to the elements, at a given point on the respective path, is proportional to an angle which is formed between a lateral direction of the article and a tangent of the respective path at the given point.

10. The article according to claim 1, wherein the elastic elements are continuously or intermittently joined to a side of the fluid-barrier layer which faces the absorbent core.

11. The article according to claim 1, wherein the elastic elements are continuously or intermittently joined to a side of the inner fluid-permeable layer which faces the absorbent core.

12. The article according to claim 1, wherein an outer layer covers a side of the article which faces away from the user during use, and in that the elastic elements are continuously or intermittently joined to a side of said outer layer which faces the absorbent core.

13. The article according to claim 1, wherein said at least four different paths are continuously curving paths.

* * * * *